United States Patent [19]

Kinlen et al.

[11] Patent Number: 4,818,365

[45] Date of Patent: Apr. 4, 1989

[54] SOLID STATE INDICATOR ELECTRODE AND METHOD OF MAKING SAME

[75] Inventors: Patrick J. Kinlen, High Ridge; John E. Heider, Maryland Heights, both of Mo.

[73] Assignee: Monsanto Company, St. Louis, Mo.

[21] Appl. No.: 918,201

[22] Filed: Oct. 14, 1986

[51] Int. Cl.[4] .............................................. G01N 27/30
[52] U.S. Cl. ................................... 204/433; 204/1 T; 427/126.5
[58] Field of Search .................. 204/433, 418, 290 R, 204/1 H; 427/126.5

[56] References Cited

U.S. PATENT DOCUMENTS 3,905,889  9/1975  Macur et al. ........................ 204/415
4,089,759  5/1978  Krumpelt et al. ..................... 204/98
4,459,324  7/1984  Gauger et al. ......................... 427/86
4,536,274  8/1985  Papadakis et al. .................. 204/433

OTHER PUBLICATIONS

Gerhardt et al., Brain Research, 290, 390-395, (1984).
Nagy et al., J. Electroanal. Chem., 188, 85-94, (1985).

*Primary Examiner*—G. L. Kaplan
*Attorney, Agent, or Firm*—Linda L. Lewis; James W. Williams, Jr.; Arnold H. Cole

[57] ABSTRACT

A junction-type metal/metal oxide solid state indicator electrode wherein the sensing portion of the electrode is coated with a perfluorocarbon copolymer, and a pH sensor made of the indicator electrode and a reference electrode.

18 Claims, 4 Drawing Sheets

SOLID STATE INDICATOR ELECTRODE AND METHOD OF MAKING SAME

FIELD OF INVENTION

This invention relates to a junction-type, metal/metal oxide solid state indicator electrode with a cation exchange polymer coating on the sensing portion of the electrode and to a process for making the electrode. The indicator electrode is used in combination with a reference electrode as a pH sensor.

DESCRIPTION OF THE RELEVANT ART

Electrolytic sensors for detecting and measuring the pH of a liquid system (a measurement of the hydrogen-ion activity) are well known. Generally such pH sensors include a glass membrane electrode and a reference electrode. The glass electrodes tend to be quite fragile, and are therefore not generally suitable for applications where the electrodes are subjected to a considerable amount of movement, jostling or shock, or high temperatures or pressures.

Junction-type metal/metal oxide solid state pH electrodes have been proposed for sensing the pH of solutions and other fluids. These electrodes have the advantage of stability in aqueous solutions over a wide range of temperatures and pressures, low impedance and fast response to pH changes. Fog et al, "Electronic Semiconducting Oxides as pH Sensors", *Sensors and Actuators*, 5 (1984) 137–146, discuss the limitations of such pH sensors. Oxidizing and reducing agents, such as ferricyanide, and hydrogen peroxide were found to interfere with pH measurement. In addition, pH sensors which utilize the junction-type electrodes discussed therein, retain the limitations of the glass electrodes discussed above, when coupled with a conventional reference electrode.

Various improvements have been made on the junction-type electrode to make it more rugged and compact.

U.S. Pat. No. 3,905,889 discloses a pH sensor in which the reference and indicator electrodes are surrounded by an electrolyte and encased in a hydrogen ion and carbon dioxide permeable diffusion barrier, such as poly(siloxane)-poly(bisphenol-A) polycarbonate block copolymer. The effective pH range for this probe is very limited, from 5.6 to 7.1.

U.S. Pat. No. 4,536,274 discloses a transcutaneous blood carbon dioxide sensor which utilizes a junction-type electrode of palladium/palladium oxide and a silver/silver halide electrode applied to an electrically nonconductive substrate, partially coated with an insulated dielectric and partially coated with any of a number of polymeric membrane materials, including perfluorocarbon copolymers. This pH sensor is limited to measuring a narrow pH range of from 6.49 to 8.50, and is characterized by slow responsiveness and poor reproducibility.

SUMMARY OF THE INVENTION

The present invention involves a junction-type, metal/metal oxide solid state indicator electrode, having a sensing portion and a method for making such electrode. The sensing portion has a perfluorocarbon copolymer coating.

The electrode can be made by the method comprising:

(a) contacting a junction-type metal/metal oxide electrode with a perfluorocarbon copolymer to form a copolymer-coated electrode,
(b) drying the coated electrode,
(c) repeating (a) and (b) to form a sufficiently coated electrode,
(d) curing the copolymer coating,
(e) cooling the electrode, and
(f) hydrating the copolymer coating.

DETAILED DESCRIPTION OF THE INVENTION

Figure 1:
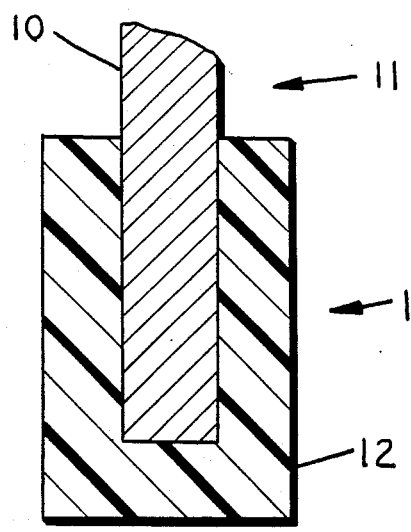
FIG. 1 is a cut away view of an indicator electrode made in accordance with this invention.

Referring to the drawings, FIG. 1 depicts a cut away of an indicator electrode 1 made in accordance with the present invention. The electrode (1) consists of a junction-type metal/metal oxide electrode (10) having a sensing portion wherein the sensing portion is coated with a perfluorocarbon copolymer (12.) The electrode has a zone (11) for electrial contact.

In a preferred embodiment, a pH sensor is prepared wherein the indicator electrode is used in conjunction with the reference electrode described in copending application Ser. No. 929,879 wherein the reference electrode is a metal/metal salt electrode, with an immobilized electrolyte in contact with the metal/metal salt electrode, and the immobilized electrolyte is coated with a perfluorocarbon copolymer which is hereby incorporated by reference. Such an embodiment is shown in FIG. 2.

Figure 2:
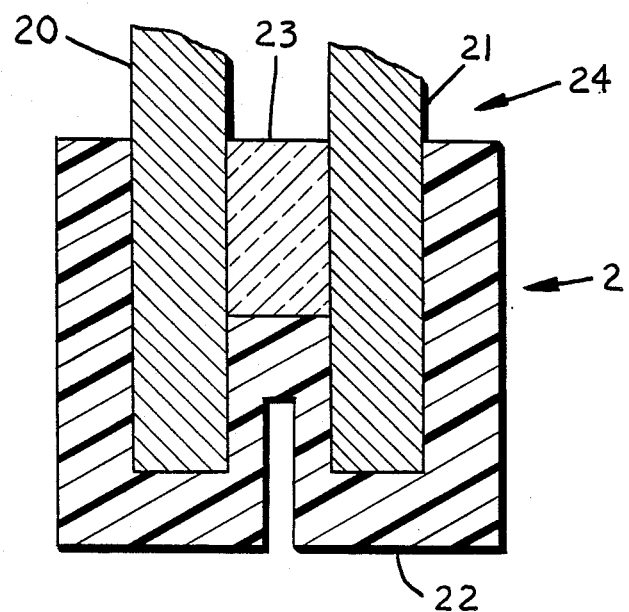
FIG. 2 is a cut away view of a pH sensor utilizing the indicator electrode in accordance with this invention.

Referring to FIG. 2, a cut away view of pH sensor (2), the indicator electrode (20) is a junction-type, metal/metal oxide electrode. The reference electrode (21) is a metal/metal salt electrode in contact with an immobilized electrolyte. A support of electrically nonconductive material (23) produces a non-conducting barrier between the indicator electrode (20) and the reference electrode (21). The nonconductive support (23) can be any material that is substantially electrically nonconductive, such as a ceramic, refractory or thermoplastic material, or a thermosetting resin.

The combination of the indicator electrode and the reference electrode, with the nonconductive support form a pH sensor. The sensing portion of the pH sensor is coated with a perfluorocarbon copolymer (22), described in detail hereinafter. The sensor has a zone (24) for electrical contact. The electrodes (20) and (21) together define an electrical potential between them when contacted with a solution or electrolyte. By measuring the electrical potential difference between the indicator electrode (20) and the reference electrode (21) at the zone (24) for electrical contact, as the probe is successively immersed in electrolytes of a different pH, a relationship between a voltage difference between electrodes (20) and (21) and the pH of a particular electrolyte in contact with the electrodes can be established. The pH of electrolytes can be determined from this voltage difference.

Although the electrode of the embodiment shown in FIGS. 1 and 2 is elongated, shape is of no particular importance. The junction-type metal/metal oxide indicator electrode (10) can be any suitable or conventional junction-type electrode made of a conducting metal having a single stable oxidation state at the particular temperature at which the active electrode is to be operated for pH sensing. Preferably this metal/metal oxide electrode is relatively immune to corrosive effects of electrolytes or other substances likely to be encountered by the active electrode while in use. Suitable metal/metal oxide combinations are palladium/palladium oxide, rhodium/rhodium oxide, ruthenium/ruthenium oxide, osmium/osmium oxide, iridium/iridium oxide, platinum/ platinum oxide, tin/tin oxide, antimony/antimony oxide, lead/lead oxide and bismuth/bismuth oxide or any combination or mixture of such metals and their oxides. In a preferred embodiment the indicator electrode metal/metal oxide is titanium/iridium oxide.

The perfluorocarbon copolymers (12) and (22) are cation exchange polymers which act as a barrier to the migration of anions to the electrode which can cause interferences when measuring pH. Such interferences are characterized by scatter in pH data or no response of the electrode with change in pH. Suitable copolymers comprise at least two monomers with one monomer being selected from a group including vinyl fluoride, hexafluoropropylene, vinylidene fluoride, trifluoroethylene, chlorotrifluoroethylene, perfluoro(alkylvinyl ether), tetrafluoroethylene, and mixtures thereof.

The second monomer contains an $SO_2F$ or COF group. Examples of such second monomers can be represented by the formula $CF_2=CFR_1SO_2F$ or $CF_2=CFR_1COF$. $R_1$ in the generic formula is a bifunctional perfluorinated radical having from 1 to 25 carbon atoms. A preferred monomer has from 1 to 8 carbon atoms. One restraint upon the generic formula is a requirement for the presence of at least one fluorine atom on the carbon atom adjacent the $—SO_2$ or COF group. The $R_1$ generic formula portion can be of any suitable or conventional configuration, but it has been found preferably that the vinyl radical comonomer join the $R_1$ group through an ether linkage.

Typical sulfonyl or carbonyl fluoride containing monomers are set forth in U.S. Pat. Nos. 3,282,875; 3,041,317; 3,560,568; 3,718,627 and methods of preparation of intermediate perfluorocarbon copolymers are set forth in U.S. Pat. Nos. 3,041,317; 2,393,967; 2,559,752 and 2,593,583.

Suitable perfluorocarbon copolymers are commercially available from E. I. duPont under the trademark Nafion ® or Dow Chemical under the trademark PFSA ®.

Coating the sensing portion of the indicator electrode with crosslinked polymers such as crosslinked acrylate copolymers made by photopolymerization of lithium acrylate, or hydrogels of polymethacrylate acid or polyacrylic acid produces an indicator electrode which yields inaccurate pH readings because of interferences due to anion migration to the electrode.

The electrode includes an area or zone (11) whereby electrical contact may be made between the electrode and sensing instrumentation. Typically, these contact areas are electrically insulated and water-proofed. Any suitable or conventional electrical device for measuring electrical output, or for comparing electrical output of the indicator electrode to a reference electrode may be used. Typically, a pH probe using the indicator electrode of the present invention would produce electrochemical potentials ranging from $-1.00$ volts to $+1.00$ volts depending on the pH of the particular electrolyte. An electrical sensing device used with the present invention must be capable of distinguishing small voltage changes used in that range.

The indicator electrode of the present invention can be used in combination with any of a number of conventional reference electrodes as a pH sensor. Such reference electrodes include a standard calomel electrode and a silver/silver chloride electrode. Other reference electrodes that can be used with the indicator electrode of the present invention are disclosed in "Reference Electrodes, Theory and Practice", Ives, D. J. G. and Janz, D. J., Academic Press, 1961, which is hereby incorporated by reference.

Preparation of the Indicator Electrode

The process for preparing the indicator electrode involves contacting a junction-type, metal/metal oxide electrode with a perfluorocarbon copolymer in an amount sufficient to coat the sensing portion of the electrode. The coating is then dried. The coating and drying steps can be repeated as required to produce a coating which acts as a barrier for migration of anions to the electrode. The coating on the electrode is then cured, cooled, and finally the copolymer coating is hydrated. The electrode can be contacted with the perfluorocarbon copolymer by methods such as spraying, vacuum depositing or dipping. In a preferred embodiment, an electrode is coated by dipping into a solution of about 5% to about 15% by weight of Nafion ® perfluorocarbon copolymer of 1100 equivalent weight in a low aliphatic alcohol and water. The electrode is then dried by any appropriate means to remove the solvent, such as heating, air drying at room temperature, or drying in a desiccator. If heating to dry, the temperature should not be raised above about 120° C. so as not to disturb the molecular configuration of the polymer. The preferred means of drying is to heat the electrode in the range of 80° C. to about 120° C. for about 30 to 90 minutes. The coating procedure is repeated until the electrode is completely coated with a thin film which is not thick enough to inhibit the responsiveness of the electrode, but sufficient to completely cover the electrode. The preferred number of coats is in the range of 2 to 5, the most preferred number of coats is 3 to 4.

The coated electrode is cured by heating or irradiating the electrode. When cured by heating, a temperature sufficient to allow a change in molecular configuration of the polymer which provides improved rejection of interferences must be reached. Although the mechanism of the curing and improved rejection of interferences due to anion migration is not understood, it is theorized that annealing of the polymer produces a better defined domain structure. The preferred method of curing involves heating the coated electrode in an oven at room temperature and slowly raising the oven temperature to a maximum temperature of about 280° C. for a period of time sufficient to cure. If the polymer is subjected to a temperature in excess of about 300°, degradation of the polymer occurs. If the polymer is subjected to a temperature of less than about 120°, or heated an insufficient time, the polymer will not cure. The most preferred maximum temperature range is about 180° C. to 230° C. The preferred time for maintaining the maximum temperature is about 15 to 60 minutes. The electrode is cooled by any conventional means that allows slow cooling. The preferred method is by turning off the oven and allowing the electrode to cool slowly to room temperature in the oven over a period of about 30 to 90 minutes. If cooled too quickly, the electrode may not properly cure because rapid cooling may cause contraction and cracking or crystallization of the polymer coating.

Proper coating and curing of the electrode can be tested by cyclic voltammetry (CV) in the presence of ferricyanide. An untreated or improperly treated electrode will show a reversible CV for the reduction of ferricyanide to ferrocyanide caused by migration of the anion to the electrode. An electrode prepared according to the present invention will show no reversible CV for ferricyanide, since that interference is effectively eliminated, e.g. the anion is unable to migrate to the electrode.

The coated electrode is hydrated by means such as soaking, heating, steaming or boiling in a liquid or vapor such as water, water solutions or buffer solutions. In a preferred embodiment, the electrode is heated in a boiling buffer solution. The most preferred method is to boil the electrode in a 0.1M solution of phosphate buffer, around pH 7, for about 15 to about 45 minutes. The electrode is allowed to cool in the solution and is stored in the buffer solution. Once the electrode is hydrated, it should be kept hydrated by contacting it with a water source such as storing it immersed in water, buffer solution or other aqueous solutions. Other water sources include water-saturated air and steam.

The following examples are for illustrative purposes only and are not meant to limit the claimed invention in any manner.

EXAMPLES

The following is a description of the preparation of an indicator electrode according to the present invention to be used in the following Examples.

Junction-type, metal/metal oxide electrodes composed of Ti/IrO$_2$ were purchased from Englehard Corp., Specialty Metals Div., 700 Blair Rd., Carteret, N.J. 07008, and were prepared by iridium chloride decomposition on a titanium electrode.

The dry electrodes were dipped three times into 10 wt % Nafion ® perfluorocarbon copolymer 117, of 1100 equivalent weight polymer in a mixture of lower aliphatic alcohols and water, available from duPont, and dried at 100° C. subsequent to each dipping. The solution was purchased as a 5 wt. percent solution and concentrated to 10 wt. percent by evaporation. The dried electrodes were placed in a room temperature oven and the oven temperature was slowly brought up to 210° C. over a period of about 45 minutes. The electrodes were cured by heating at 210° C. for thirty minutes in the oven. The electrodes were slowly cooled to room temperature over a period of about 1 hour by turning off the oven and leaving the electrodes in it while cooling. The electrodes were placed in a pH 7 phosphate buffer solution (0.1M) and heated to boiling and boiled for thirty minutes. The buffer solution containing the electrodes was removed from heat and allowed to cool. The electrodes were stored in the solution.

The electrodes were tested using cyclic voltammetry (CV) in the presence of ferricyanide, and the reversible CV for the reduction of ferricyanide to ferrocyanide was effectively eliminated as an interference, e.g. migration of the Fe(CN)$_6^{-4}$ anion to the electrode was prevented.

EXAMPLE 1

Figure 3A:
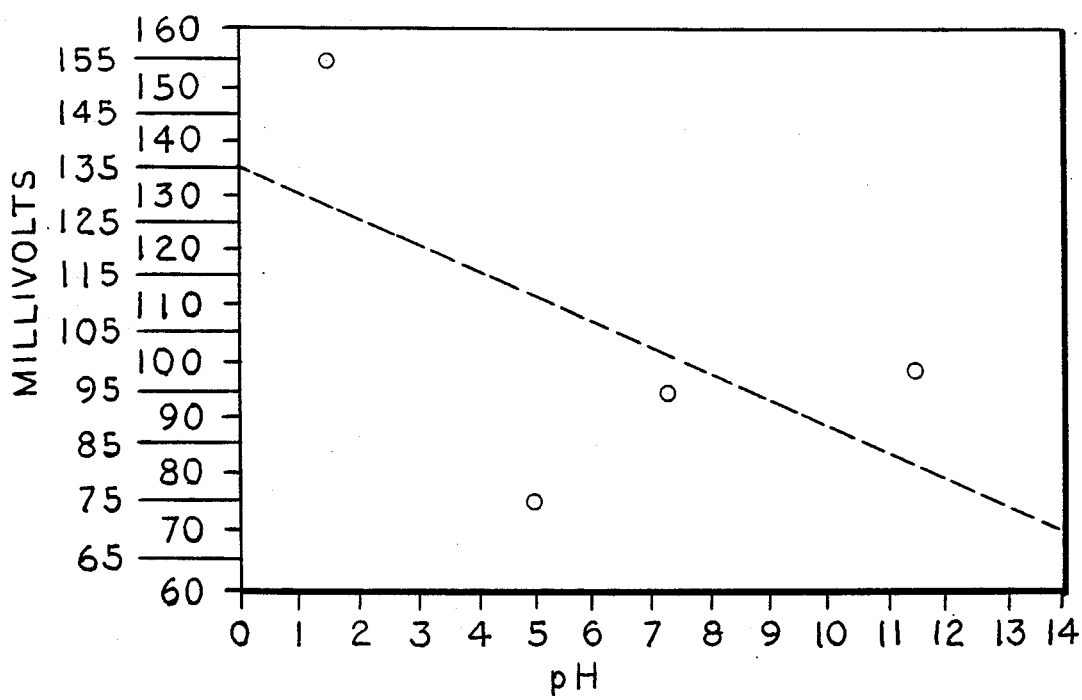
FIG. 3A is a graphical representation of a voltage output from a sensor made from an uncoated metal/metal oxide electrode plotted against pH for a titration of 0.1M $H_3PO_4$ and 0.01M $K_4Fe(CN)_6$ with 1M NaOH.
Figure 3B:
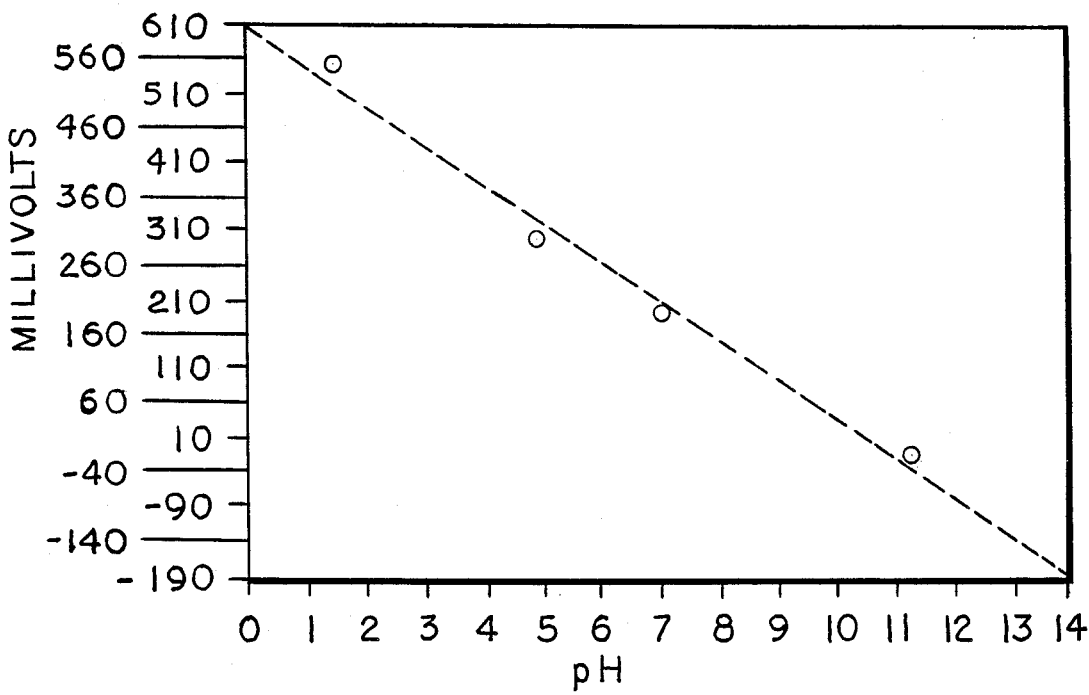
FIG. 3B is a graphical representation of a voltage output from a sensor made with an electrode in accordance with this invention plotted against pH for a titration of 0.1M $H_3PO_4$ and 0.01M $K_4Fe(CN)_6$ with 1M NaOH.

The indicator electrode according to the present invention was prepared by the method described above. It was used with a standard calomel electrode as a pH sensor. Data were generated by the titration of 0.1M H$_3$PO$_4$ containing 0.01M K$_4$Fe(CN)$_6$, an oxidant that normally interferes with pH detection when metal/metal oxide electrodes are used, with 1M NaOH, in a pH range of 1.5 to 12.0. The pH was plotted versus voltage (millivolts). The plot of FIG. 3(A) is generated by the above titration using a bare electrode and the plot of FIG. 3(B) is generated using the coated electrode of the present invention. There is a large difference between the plots generated by bare electrode, shown in FIG. 3(A), which has a great deal of scatter, and the plot generated by the coated electrode of the present invention, shown in FIG. 3(B), which is essentially linear and where the interference due to anion migration is eliminated.

EXAMPLE 2

Figure 4A:
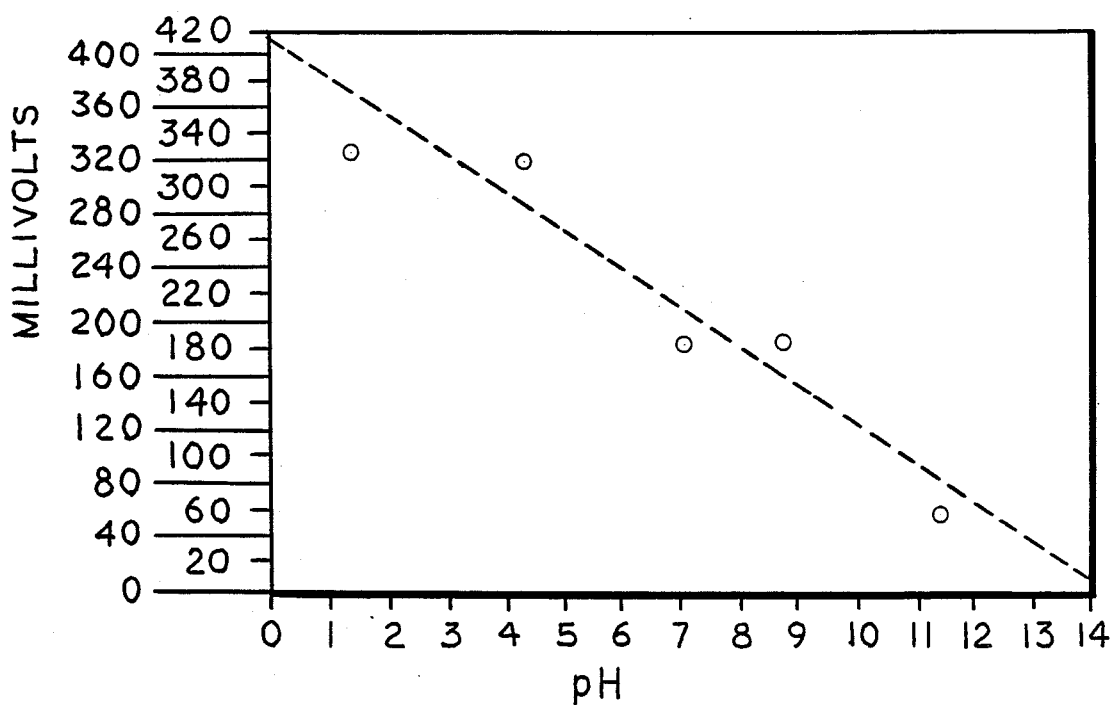
FIG. 4A is a graphical representation of a voltage output from a sensor made from an uncoated metal/metal oxide electrode plotted against pH for a titration of 0.1M $H_3PO_4$ and 0.1M KI with 1M NaOH.
Figure 4B:
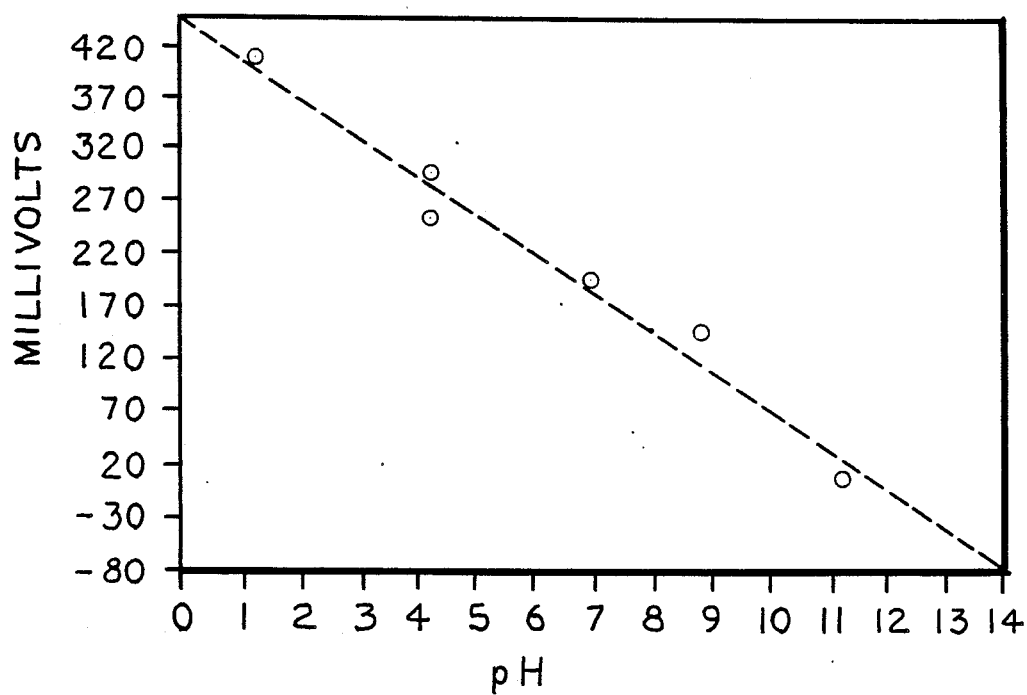
FIG. 4B is a graphical representation of a voltage output from a sensor made with an electrode in accordance with this invention plotted against pH for a titration of 0.1M $H_3PO_4$ and 0.1M KI with 1M NaOH.

The same procedure was used as was in Example 1, except that the 0.1M H$_3$PO$_4$ solution contained 0.01M KI rather than K$_4$Fe(CN)$_6$, an ion that also normally interferes with pH detection when metal/metal oxide electrodes are used. FIGS. 4A and 4B show plots generated by titration with 1M NaOH. The plot generated by titration using the bare electrode, shown in FIG. 4(A), has scatter, while the plot generated by the coated electrode of the present invention, shown in FIG. 4(B), has little scatter since the interferance due to anion migration is eliminated.

Figure 5A:
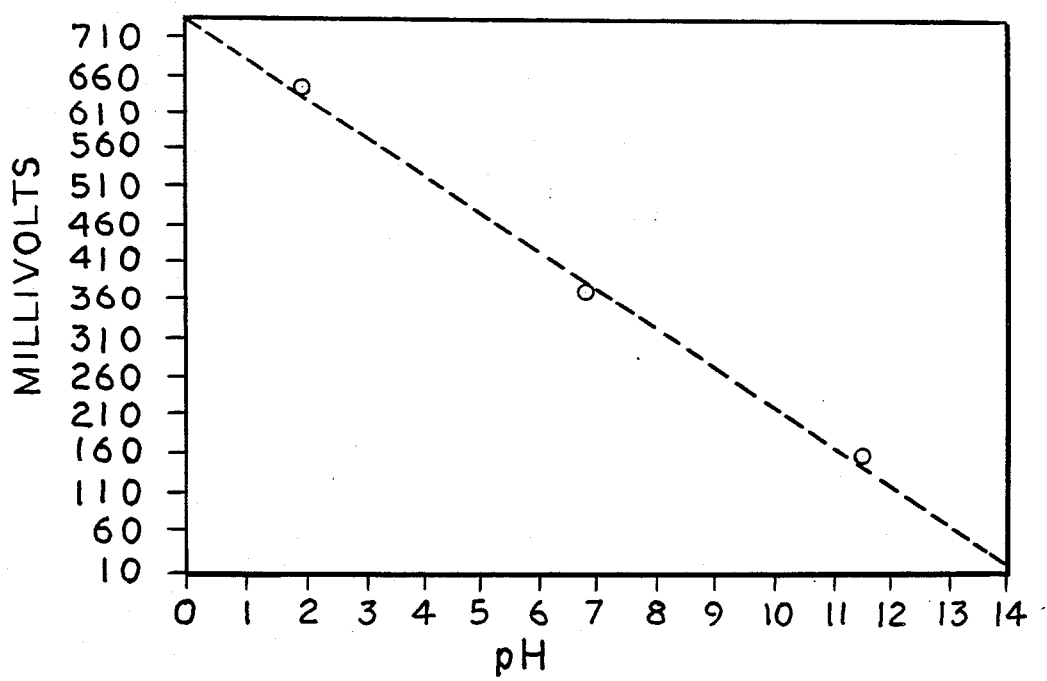
FIG. 5A is a graphical representation of a voltage output plotted against pH for a titration of 0.1M $H_3PO_4$ with 1M NaOH from a sensor made from an uncoated metal/metal oxide electrode utilizing an indicator electrode not in accordance with this invention.
Figure 5B:
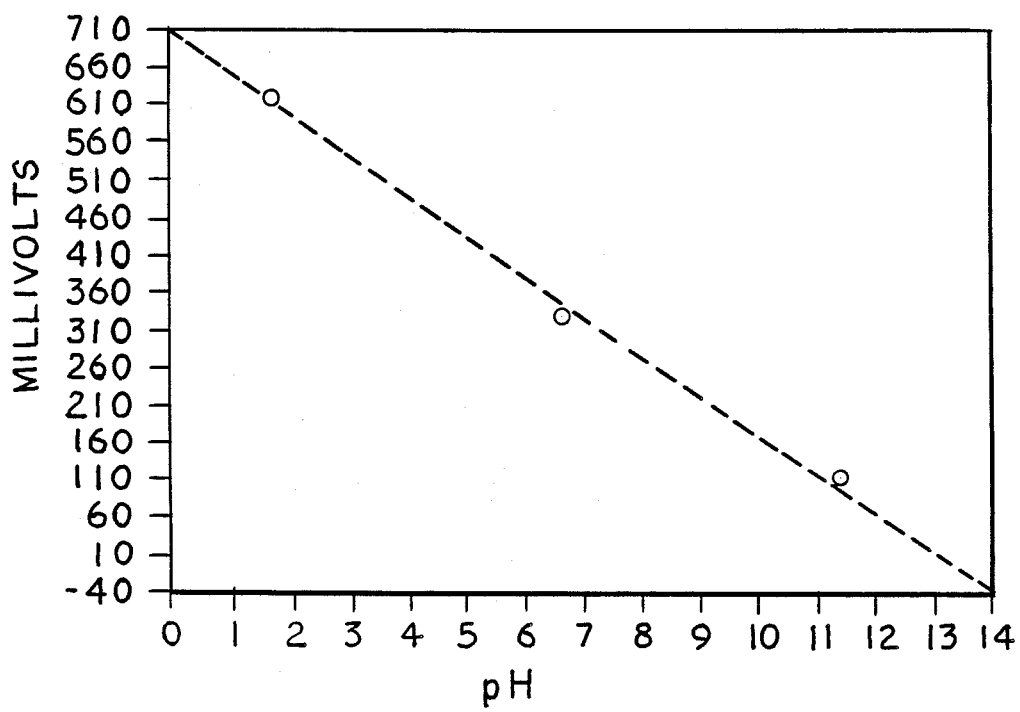
FIG. 5B is a graphical representation of a voltage output plotted against pH for a titration of 0.1M $H_3PO_4$ with 1M NaOH obtained utilizing the indicator electrode in accordance with this invention.

In a similar procedure as was used as in Example 1, no interfering ions were present in the H$_3$PO$_4$ solution. FIGS. 5(A) and 5(B) show plots generated by titration with 1M NaOH. In the absence of interfering ions, both electrodes work equally showing very little scatter.

Control 1

Indicator electrodes were prepared by dip coating titanium/iridium oxide electrodes in a 10% by weight solution of polymethacrylic acid and drying by air at 50° C. The electrode was then dipped into a 0.12M solution of hexamethylene diamine in water to achieve crosslinking at the surface. The electrode was dried at 50° C. The above two-dip process was repeated, and the electrode was stored in water. Upon testing by cyclic voltammetry (CV) in the presence of ferricyanide, a reversible CV for the reduction of ferricyanide to ferrocyanide was observed, indicating that migration of the anion to the electrode had occurred and that the interference was not eliminated.

We claim:

1. A junction-type metal/metal oxide solid state indicator electrode having improved rejection of interferences caused by anion migration comprising a sensing portion, wherein the sensing portion has a cured perfluorocarbon copolymer coating.

2. The solid state indicator electrode of claim 1 wherein the metal/metal oxide is selected from the group consisting of palladium/palladium oxide, iridium/iridium oxide and titanium/iridium oxide.

3. The solid state indicator electrode of claim 1 wherein the perfluorocarbon copolymer is a copolymer of at least two monomers wherein one monomer is selected from a group consisting of vinyl fluoride, hexafluoropropylene, vinylidene fluoride, trifluoroethylene, chlorotrifluoroethylene, perfluoro-(alkylvinyl ether) and tetrafluoroethylene and tetrafluoroethylene and the second monomer is selected from a group of monomers containing an $SO_2F$ or COF group.

4. The solid state indicator electrode of claim 3 where the metal/metal oxide-junction-type electrode is titanium/iridium oxide.

5. A method for making a junction-type metal/metal oxide solid state indicator electrode comprising the steps:
   (a) contacting the electrode with a perfluorocarbon copolymer to form a copolymer-coated electrode,
   (b) drying the coated electrode,
   (c) repeating (a) and (b) from 2 to 5 times, to form a sufficiently coated electrode,
   (d) curing the copolymer coating,
   (e) cooling the electrode, and
   (f) hydrating the copolymer coating.

6. The method of claim 5 wherein the metal/metal oxide is selected from the group consisting of palladium/palladium oxide, iridium/iridium oxide and titanium/iridium oxide.

7. The method of claim 5 wherein the perfluorocarbon copolymer is a copolymer of two or more monomers wherein one monomer is selected from a group consisting of vinyl fluoride, hexafluoropropylene, vinylidene fluoride, trifluoroethylene, chlorotrifluoroethylene, perfluoro-(alkylvinyl ether) and tetrafluoroethylene and the second monomer is selected from a group of monomers containing an $SO_2F$ or COF group.

8. The method of claim 5 wherein the electrode is contacted with a perfluorocarbon copolymer by dip coating 2 to 5 times in about a 5% to 15% by weight solution of the perfluorocarbon copolymer and dried at about 80° C. to 120° C. for about 30 to 90 minutes.

9. The method of claim 8 wherein the copolymer coating of the junction-type electrode is cured by heating in the range of about 180° C. to 230° C. for about 15 to 60 minutes and cooled to room temperature over a period of about 30 to 90 minutes.

10. The method of claim 9 wherein the copolymer coating of the electrode is hydrated by boiling in a buffer solution for about 15 to about 45 minutes.

11. The solid state electrode made according to the method of claim 5.

12. A method to make a junction-type metal/metal oxide solid state indicator electrode having improved rejection of interferences causes by anion migration comprising the steps:
   (a) dip coating the electrode in a solution or suspension containing about 5% to 15% by weight of a perfluorocarbon copolymer to form a copolymer-coated electrode,
   (b) drying the coated electrode at about 80° C. to 120° C. for about 30 to 90 minutes,
   (c) repeating (a) and (b) from 2 to 5 times to form a sufficiently coated electrode,
   (d) heating to cure the coated electrode in the range of about 180° to 230° C. for about 30 to 90 minutes,
   (e) cooling the electrode to room temperature over a period of about 30 to 90 minutes, and
   (f) hydrating the copolymer coating of the electrode by boiling in a buffer solution for about 15 to about 45 minutes, wherein the perfluorocarbon copolymer is a copolymer of at least two monomers wherein one monomer is selected from a group consisting of vinyl fluoride, hexafluoropropylene, vinylidene fluoride, trifluoethylene, chlorotrifluoroethylene, perfluoro-(alkylvinyl ether) and tetrafluoroethylene and the second monomer is selected from a group of monomers containing an $SO_2F$ or COF group.

13. A pH sensor having improved rejection of interferences comprising:
   (a) a junction-type metal/metal oxide solid state indicator electrode having a sensing portion, wherein the sensing portion has a cured perfluorocarbon copolymer coating, in combination with
   (b) a reference electrode.

14. The pH sensor of claim 13 wherein the reference electrode is selected from the group consisting of standard calomel electrodes and Ag/AgCl electrodes.

15. The pH sensor of claim 13 wherein the reference electrode is a metal/metal salt electrode comprising an immobilized electrolyte in contact with the metal/metal salt electrode wherein the immobilized electrolyte has a perfluorocarbon copolymer coating.

16. The pH sensor of claim 13 wherein the metal/metal oxide is selected from the group consisting of palladium/palladium oxide, iridium/iridium oxide and titanium/iridium oxide.

17. The pH sensor of claim 13 wherein the perfluorocarbon copolymer is a copolymer of at least two monomers wherein one monomer is selected from a group consisting of vinyl fluoride, hexafluoropropylene, vinylidene fluoride, trifluoroethylene, chlorotrifluoroethylene, perfluoro-(alkylvinyl ether) and tetrafluoroethylene and the second monomer is selected from a group of monomers containing an $SO^2F$ or COF group.

18. A pH sensor having improved rejection of interferences and a sensing portion and a support of electrically non-conductor material comprising:
   (a) a junction-type metal/metal oxide solid state indicator electrode in contact with the support, in combination with
   (b) a Ag/AgCl reference electrode in contact with the support wherein the reference electrode has an immobilized chloride in contact with the Ag/AgCl, and
   (c) a coating of a cured perfluorocarbon copolymer over the sensing portion of the pH sensor, wherein the perfluorocarbon copolymer is a copolymer of at least two monomers wherein one monomer is selected from a group consisting of vinyl fluoride, hexafluoropropylene, vinylidene fluoride, trifluoroethylene, chlorotrifluoroethylene, per- fluoroalkylvinyl ether), and tetrafluoroethylene and the second monomer is selected from a group of monomers containing an $SO_2F$ group.

* * * * *